(12) United States Patent
Nakajima et al.

(10) Patent No.: US 8,404,888 B2
(45) Date of Patent: Mar. 26, 2013

(54) PROCESS FOR PRODUCING ACRYLIC ACID

(75) Inventors: Akiyoshi Nakajima, Kobe (JP); Naohiro Fukumoto, Aioi (JP)

(73) Assignee: Nippon Shokubai Co., Ltd., Osaka (JP)

( * ) Notice: Subject to any disclaimer, the term of this patent is extended or adjusted under 35 U.S.C. 154(b) by 355 days.

(21) Appl. No.: 12/733,393

(22) PCT Filed: Jul. 24, 2008

(86) PCT No.: PCT/JP2008/063708
§ 371 (c)(1), (2), (4) Date: Feb. 26, 2010

(87) PCT Pub. No.: WO2009/028292
PCT Pub. Date: Mar. 5, 2009

(65) Prior Publication Data
US 2010/0174112 A1 Jul. 8, 2010

(30) Foreign Application Priority Data
Aug. 30, 2007 (JP) ................. 2007-224035

(51) Int. Cl.
*C07C 51/16* (2006.01)
(52) U.S. Cl. ..................................... 562/545
(58) Field of Classification Search .......... 562/545, 562/547
See application file for complete search history.

(56) References Cited

U.S. PATENT DOCUMENTS

| 6,388,129 | B1 | 5/2002 | Machhammer et al. |
| 6,423,875 | B1 | 7/2002 | Machhammer et al. |
| 6,426,433 | B1 | 7/2002 | Machhammer et al. |
| 6,492,548 | B1 * | 12/2002 | Brockwell et al. ............ 562/545 |
| 2005/0137422 | A1 | 6/2005 | Hazin et al. |
| 2007/0117998 | A1 | 5/2007 | Machhammer et al. |

FOREIGN PATENT DOCUMENTS

| EP | 0 117 146 | 8/1984 |
| EP | 1 193 240 | 4/2002 |
| GB | 2 118 939 | 11/1983 |
| JP | 2000-502719 | 3/2000 |
| JP | 2002-523387 | 7/2002 |
| JP | 2002-523389 | 7/2002 |
| JP | 2002-523390 | 7/2002 |

OTHER PUBLICATIONS

International Search Report issued Nov. 27, 2008 in International (PCT) Application No. PCT/JP2008/063708.
Written Opinion issued Nov. 27, 2008 in International (PCT) Application No. PCT/JP2008/063708.

* cited by examiner

*Primary Examiner* — Taylor Victor Oh
(74) *Attorney, Agent, or Firm* — Wenderoth, Lind & Ponack, L.L.P.

(57) ABSTRACT

A process which enables production of acrylic acid on an industrial scale at high productivity with stability, comprising production of acrylic acid by oxidation of propane with molecular oxygen, is provided. The process is characterized in characterized by re-use of the gas containing unreacted propane, as obtained after recovering acrylic acid from the gas produced of the reaction, as a recycling gas after removing at least a part of carbon dioxide from the same gas.

5 Claims, No Drawings

PROCESS FOR PRODUCING ACRYLIC ACID

TECHNICAL FIELD

This invention relates to a process for producing acrylic acid by catalytic gas phase oxidation of propane with molecular oxygen. More specifically, the invention relates to a process for producing acrylic acid at high productivity with stability, which comprises oxidizing and dehydrogenating propane in the presence of molecular oxygen to produce propylene, and catalytically oxidizing the resulting propylene at gas phase.

BACKGROUND TECHNOLOGY

Catalytic gas phase oxidation processes of propylene with molecular oxygen has been widely adopted for industrial production of acrylic acid. In particular, two-stage oxidation processes comprising the first oxidation step of catalytically oxidizing propylene at gas phase to form acrolein and the second oxidation step of catalytically oxidizing the resulting acrolein at gas phase to produce acrylic acid are in the mainstream.

Acrylic acid is broadly utilized as a starting material for its esters, polymers and the like, and is an important industrial product. In these years demand for a water absorbent resin prepared from acrylic acid as the starting material is increasing, and in consequence demand for acrylic acid also is increasing.

A water absorbent resin is a water-swellable and water-insoluble polyacrylic acid having crosslinked structure, which can be obtained by crosslinking polymerization of acrylic acid and/or salt thereof as the base monomer (preferably at least 70 mol %, in particular, at least 90 mol %) using further about 0.001-5 mol % (to the acrylic acid) of a crosslinking agent and about 0.001-2 mol % to the acrylic acid of a radical polymerization initiator, followed by drying and pulverization of the product. The resin absorbs at least three times, preferably 10-1,000 times, its own weight of pure water or physiological saline solution to form water-insoluble hydrogel containing no more than 25 mass %, preferably no more than 10 mass %, of water-soluble component (water-soluble substance).

On the other hand, propylene, the starting material, also is a starting material of polypropylene, acrylonitrile and the like, and the need therefor is yearly increasing. In consequence, it is predicted that the propylene supply as the starting material of acrylic acid will become unable to catch up with the demand and there is a possibility of propylene shortage. With the view to cope with this, investigations for production process of acrylic acid using cheap and readily available propane as the starting material are vigorously made in recent years.

As to production processes for acrylic acid from propane as the starting material, various proposals have been made, such as oxidation of propane to directly produce acrylic acid, or first producing propylene by simple dehydrogenation or oxidative dehydrogenation of propane and producing acrylic acid from the resulting propylene by the two-stage oxidation process. None of those proposals is yet satisfactory for industrial scale working, however, and improvements are desired.

For example, as for the process comprising oxidative dehydrogenation of propane to produce propylene and the two-stage oxidation of the propylene to produce acrylic acid, various trials are made including suppressing propane conversion to a relatively low level in order to maintain high propylene selectivity in the oxidative dehydrogenation step and after the subsequent production of acrylic acid from the so formed propylene via acrolein in the presence of unreacted propane, recycling the unreacted propane for re-use.

JP 2000-502719A discloses that use of air as the oxygen source involves a possibility for the nitrogen in the air to adversely affect the recycling of the discharged gas, and hence it is preferable to use an oxygen source whose oxygen content is at least 90%.

Whereas, JP 2002-523387A proposes to use air as the source of the oxygen supply and to separate at least a part of the molecular nitrogen which is contained in the recycled gas. Also JP 2002-523389A and 2002-523390A propose to use modified air having a less nitrogen content and more oxygen content than those of air, as the source of oxygen supply, and to separate at least a part of the molecular nitrogen contained in the recycled gas.

DISCLOSURE OF THE INVENTION

These processes, however, cannot be yet said fully satisfactory for industrial scale working and leave room for improvement.

The process of JP 2000-502719A pays attention to the oxygen supply source only. Sufficient improvement cannot be attained by such a process because the gas to be recycled contains, besides unreacted propane, side-products of the oxidation reaction which gradually accumulate in the reaction system with the recycling and cause gradual changes in the amount and composition of the gas in the reaction system, rendering stable reaction impossible. Also the processes of JP 2002-523387A, 2002-523389A and 2002-523390A remove nitrogen from the gas to be recycled but do not remove the side reaction products which gradually accumulate in the reaction system to induce changes in composition of the reaction gas. Again, because the reaction gas contains nitrogen, the amount of the gas passing through the reaction system increases, consequently giving rise to such problems as enlargement of facilities such as the reactor and the like and increase in energy consumption by blowers.

This invention aims at provision of a process which enables production of acrylic acid on an industrial scale with high productivity and stability, in occasion of producing acrylic acid from propane as the starting material.

We discovered that the above problems could be solved by a process of producing acrylic acid by catalytic gas phase oxidation of propane with molecular oxygen wherein, in the occasion of re-using the unreacted propane-containing gas left after recovering acrylic acid from the gas formed of the reaction, as the recycling gas, removing at least a part of carbon dioxide present in the recycling gas.

INDUSTRIAL UTILIZABILITY

According to the invention, the optimum reaction condition can be stably created in consequence of controlling the carbon dioxide content of the recycling gas, which enables effective utilization of the starting propane, operation using relatively compact size facilities with low energy consumption and acrylic acid production at high productivity.

THE BEST MODE FOR WORKING THE INVENTION

According to the invention, a process for producing acrylic acid is provided, of which favorable embodiment is characterized by comprising the following steps (a)-(f):

(a) an oxidative dehydrogenation step of passing a gaseous starting mixture containing propane and molecular oxygen through a propylene synthesis zone to form a first flow containing unreacted propane and propylene;

(b) a first oxidation step of passing the first flow through an acrolein synthesis zone to form a second flow containing acrolein;

(c) a second oxidation step of passing the second flow through an acrylic acid synthesis zone to form a third flow containing acrylic acid;

(d) an acrylic acid recovery step of separating the third flow to a liquid flow containing acrylic acid and a gaseous fourth flow containing unreacted propane and carbon dioxide;

(e) a carbon dioxide-removing step of eliminating at least a part of the carbon dioxide from the fourth flow to form a fifth flow containing unreacted propane; and (f) a recycling step of re-using at least a part of the fifth flow as a recycling gas.

Oxidative Dehydrogenation Step

In the present invention, the oxidative dehydrogenation step of propane can be carried out in gas phase, using molecular oxygen in the presence of a homogeneous and/or heterogeneous catalyst system. As the supply source of molecular oxygen, preferably modified air whose oxygen concentration is raised higher than normal oxygen concentration (21 vol %) of air by selective elimination of nitrogen or like means is used, while air may be used as it is. It is preferred to use, for example, modified air having an oxygen concentration of at least 90 vol %, and more advantageously, modified air having an oxygen concentration of at least 98 vol %. If possible, it is the best to use pure oxygen.

In the oxidative dehydrogenation step of propane according to the present invention, steam is not essential, but its presence to a certain extent is preferred. Means for supplying steam is subject to no critical limitation.

The catalyst to be used for producing propylene by oxidative dehydrogenation of propane is not particularly limited but any optional catalyst can be used so long as it is effective for the pertinent reaction. For example, Co—Mo oxide catalyst (U.S. Pat. No. 4,131,631), V—Mg oxide catalyst (U.S. Pat. No. 4,777,319), Ni—Mo oxide catalyst (U.S. Pat. No. 5,063,032), $CeO_2/CeF_3$ catalyst (CN 1073893A) and Mn oxide catalyst (JP 2004-141764A) and the like are useful.

The reactor to be used in the oxidative dehydrogenation step of propane is not particularly limited, but any desired reactor can be used. It is advantageous to use a shell-and-tube fixed bed type reactor, but moving bed type reactor or fluidized bed type reactor may also be used. Again, the reactor may be one, or two or more. In the latter case, molecular oxygen-containing gas may be introduced into each of the reactors.

The conditions for the reaction for producing propylene by oxidative dehydrogenation of propane are suitably set, referring to the following conditions as the guideline. Generally there is a tendency in oxidative dehydrogenation of propane to form propylene that an increase in propane conversion notably decreases propylene selectivity, and from economic standpoint, it is necessary to maintain as high as possible propylene selectivity. On the other hand, for raising propylene selectivity, propane conversion must be suppressed as low as possible. Too low a propane conversion, however, causes the amount of the recycling gas to become enormous, consequently inviting serious losses in productivity or cost-effectiveness, e.g., a part of the unreacted propane-containing recycling gas has to be purged outside the reaction system. Thus a proper propane conversion is about 5-about 50 mol %, preferably 10-40 mol %, and a proper propylene selectivity is about 50-98 mol %, preferably 65-98 mol %.

The reaction temperature and space velocity in the propylene production by oxidative dehydrogenation of propane are not particularly limited, so long as they meet the above conditions, and the reaction conditions can be set to allow the catalyst used to exhibit its maximum performance.

The First Oxidation Step

In the first oxidation step wherein the first flow containing propylene as obtained in the oxidative dehydrogenation step of propane is passed through an acrolein synthesis zone to produce acrolein from propylene, any of those catalysts which are effective for converting propylene to acrolein can be used, not limited to any specific catalyst. For example, Mo—Bi—Fe oxide catalyst as disclosed in JP Sho 47 (1972)-42241B, JP Sho 48 (1973)-119346A can be favorably used.

Shape of those catalysts is not particularly limited, which can be, when a shell-and-tube fixed bed type reactor is used, in the form of molded catalyst made by molding catalytically active component into pellets, spheres, cylinders, rings or tablets, or supported catalyst made by supporting the catalytically active component on inert carrier, for example, alumina, silica-alumina and the like of above shapes.

The reaction gas to be introduced into the acrolein synthesis zone normally has a composition comprising 5-20 vol %, preferably 7-15 vol %, of propylene; 8-40 vol %, preferably 12-30 vol %, of molecular oxygen; 5-70 vol %, preferably 10-60 vol %, of propane; and 3-40 vol %, preferably 5-30 vol %, of carbon dioxide, the sum of the propane and carbon dioxide being 20-80 vol %, preferably 30-70 vol %. Steam can occupy 3-50 vol %, preferably 5-40 vol %, the molar ratio of the steam to propylene (steam/propylene) being 0.5-8.0, preferably 0.6-5.0. Also the molar ratio of the molecular oxygen to propylene (molecular oxygen/propylene) is within a range of 1.4-4.0, preferably 1.6-3.0.

According to the present invention, it is essential to eliminate the whole or a part of carbon dioxide in the recycling gas containing unreacted propane, so that the first flow from the oxidative dehydrogenation step can be used in the first oxidation step as it is. It is also possible to add to the first flow propane, propylene, oxygen, steam or carbon dioxide, in order to stably maintain the above-described compositional ratios in the reaction gas. For example, when propane is to be added, it is preferred to use a part of the fourth flow remaining after recovering acrylic acid from the gaseous reaction product, or further the fifth flow remaining after removing carbon dioxide from the fourth flow. Again, where carbon dioxide is to be added, the carbon dioxide isolated from the fourth flow may be used.

Adequate reaction conditions for the first oxidation step are: temperatures ranging 250-450° C., preferably 270-370° C. and contact time of 1.0-7.2 seconds, preferably 1.8-6.0 seconds.

The Second Oxidation Step

In the second oxidation step in which the acrolein-containing second flow as obtained in the first oxidation step is passed through an acrylic acid synthesis zone to form acrylic acid from acrolein, any catalyst effective for conversion of acrolein to acrylic acid can be used with no limitation to specific catalyst. For example, Mo—V oxide catalyst as described in JP Sho 49 (1974)-11371B and JP Sho 64 (1989)-85139A are suitable.

Shape of the catalyst can be suitably selected in accordance with the construction of the reactor used, and is not particularly limited. Where a shell-and-tube fixed bed type reactor is used, molded catalyst formed by molding the catalytically active component into pellets, spheres, cylinders, rings or tablets; or supported catalyst formed by supporting the catalytically active component on inert carriers such as alumina, silica-alumina and the like can be suitably used.

Adequate reaction conditions for the second oxidation step are temperatures ranging 180-350° C., preferably 200-320° C., and contact time of 1.0-7.2 seconds, preferably 1.6-6.0 seconds.

The reaction gas to be introduced into the acrylic acid synthesis zone of second oxidation step is preferably used retaining the composition of the second flow containing acrolein, as obtained in the first oxidation step. It is permissible, however, to supply thereinto molecular oxygen, where necessary. In that case, it is undesirable to use air as it is as the supply source of molecular oxygen, but preferably a modified air whose oxygen concentration is raised by, for example, selective removal of nitrogen is used. Use of such modified air having an oxygen concentration of at least 90 mol % is advantageous, in particular, use of modified air having an oxygen concentration of at least 98 mol % is still more advantageous. If all possible, use of pure oxygen is the best.

The reactor(s) used in the first oxidation step and second oxidation step are not particularly limited, while shell-and-tube fixed bed type reactor is preferred. Use of each separate reactor for each step has no detrimental effect. Whereas, a process as described in, for example, JP Hei 11 (1999)-130722A which uses one shell-and-tube fixed bed type reactor which is divided into the upper and lower parts, carrying out the first oxidation step and second oxidation step respectively at the upper and lower parts, also is suitable.

Acrylic Acid-Recovering Step

Recovery of the object product, acrylic acid, from the third flow as formed in the second oxidation step can be carried out by heretofore known methods. For example, an acrylic acid-containing liquid flow is formed by such methods as contacting the third flow as formed in the second oxidation step with a collecting solvent like water or organic solvent to cause the latter to absorb the acrylic acid, or cooling the third flow to directly condense the condensable components such as acrylic acid; and the acrylic acid is purified from the resulting acrylic acid-containing liquid flow by known means such as extraction, distillation, crystallization and the like. Thus high purity acrylic acid can be produced.

The resulting high purity acrylic acid is useful as a starting material of various esters and also as that of various polymers such as absorbent resins.

Carbon Dioxide-Removing Step

The fourth flow containing unreacted propane and carbon dioxide, as formed in the above acrylic acid-recovering step is re-used by recycling, with the view to effectively utilize the unreacted propane.

If this fourth flow is used as the recycling gas as it is, however, carbon dioxide or the like which are contained in the fourth flow besides the unreacted propane gradually accumulate in the reaction system, resulting in gradual changes in the composition or amount of the reaction gas in each of the oxidative dehydrogenation step, first oxidation step and second oxidation step, making it impossible to stably carry out the reaction over a long period.

In the present invention, the fourth flow is recycled after removing therefrom at least a part of carbon dioxide. In consequence, it becomes possible to effectively utilize the propane and to control composition of the reaction gas in each of the oxidative dehydrogenation step, first oxidation step and second oxidation step.

Removal of carbon dioxide can be effected by generally known means. For example, a method as described in JP Sho 37 (1962)-951B which uses an alkaline absorptive liquid to which boric acid, phosphoric acid, vanadic acid or the like is added; a method as described in GBP 1084526, using an alkaline absorptive liquid to which ethanolamine is added; can be used. As the alkaline absorptive liquid which absorbs carbon dioxide, for example, aqueous solutions of sodium carbonate, potassium carbonate, sodium bicarbonate, potassium bicarbonate, sodium hydroxide, potassium hydroxide, alkanolamines (monoethanolamine, diethanolamine, triethanolamine and the like), diglycolamine and the like can be used.

In the present invention, the following carbon dioxide absorption step and desorption step can be favorably used. Specifically, the steps comprise introducing the fourth flow into a carbon dioxide absorption column to cause its counter-current contact with an alkaline absorptive liquid, for example, hot aqueous potassium carbonate solution, to have the alkaline absorptive liquid to absorb carbon dioxide gas; and introducing the alkaline absorptive liquid containing the carbon dioxide into a carbon dioxide gas desorption column and desorbing and separating the carbon dioxide gas by heating the bottom portion of the desorption column. The aqueous potassium carbonate solution, from which the carbon dioxide is substantially stripped off and discharged through the top of the carbon dioxide gas desorption column, is used again as the absorptive liquid in the carbon dioxide absorption column. In certain cases it is also possible to pass the carbon dioxide-containing alkaline absorptive liquid through a flush drum before introducing it into the carbon dioxide desorption column, whereby advancedly removing gases other than carbon dioxide from the absorptive liquid. It should be noted, however, this step is not limited to the above-described method, but any method can be used so long as it can selectively remove all or a part of carbon dioxide from the fourth flow.

Adequate operation conditions of the carbon dioxide absorption column are: pressure of about 0.1-5.0 MPa, preferably 0.2-4.0 MPa, and temperature of 50-150° C., preferably 80-120° C.; and those of the carbon dioxide desorption column are: pressure not higher than about 0.5 MPa, preferably not higher than 0.2 MPa, and temperature of 50-150° C., preferably 80-120° C., respectively. Adequate operation conditions of flush drum are: pressure not higher than 1.0 MPa, preferably not higher than 0.5 MPa, and temperature of 50-150° C., preferably 80-120° C. Needless to say, the operation conditions should be so selected as to make the compositions of the reaction gases at the oxidative dehydrogenation step, first oxidation step and second oxidation step, in particular, the carbon dioxide concentration in the reaction gas to be introduced into the first oxidation step, the optimum.

Recycling Step

The fifth flow resulting from removal of at least a part of carbon dioxide from the fourth flow is recirculated as the recycling gas, to at least one of the oxidative dehydrogenation step, first oxidation step and second oxidation step, to be re-used. From the viewpoint of effective utilization of propane, the recycling gas is preferably supplied to the oxidative dehydrogenation step, concurrently with the starting gaseous mixture containing propane and molecular oxygen.

EXAMPLES

Hereinafter the present invention is explained, in further details, referring to Examples and Comparative Examples, but the invention is not limited to these Examples. In the following, the acrylic acid yield to the propane supply is determined according to the following equation:

$$\text{acrylic acid yield} = \left(\frac{\text{formed acrylic acid (mol)}}{\text{suppiled propane (mol)}}\right) \times 100$$

Example 1

—Catalysts—

As the catalyst for oxidative dehydrogenation of propane, the catalyst as disclosed in Example 1 of JP 2004-141764A was prepared. Also as the catalyst for acrolein production and that for acrylic acid production, the first stage catalyst and the second stage catalyst as disclosed in Example 1 of JP Sho 64 (1989)-63543A were prepared. Composition of the metallic elements excepting oxygen of each of the catalysts was as follows:

Catalyst for oxidative dehydrogenation of propane:
$Mn_1Sn_{0.17}Sb_{0.3}W_{0.1}Cr_{0.2}Ni_{0.2}Li_{0.02}K_{0.02}$
Catalyst for acrolein production:
$Co_4Fe_1Bi_1W_2Mo_{10}Si_{1.35}K_{0.06}$
Catalyst for acrylic acid production:
$Mo_{12}V_{4.6}Cu_{2.2}Cr_{0.6}W_{2.4}$.

—Reactions—

[The Oxidative Dehydrogenation Step]

A steel reaction tube of 25 mm in inner diameter and 3000 mm in length was charged with 1.0 L of the catalyst for oxidative dehydrogenation of propane, and heated to 460° C. Through the entrance of the reaction tube, gas (A) as formed by mixing a gaseous mixture of 46.3 vol % of propane, 53.4 vol % of oxygen and balance of argon, which was supplied at a rate of 990 L/hr (standard condition), with a recycling gas, was supplied and the reaction gas was discharged through the exit of the reaction tube. [This gas is referred to as the exit gas (B)].

[The First Oxidation Step]

A shell-and-tube reactor for the first oxidation step, comprising two steel tubes of 25 mm in inner diameter and 3000 mm in length each, was uniformly charged with 2.5 L of the catalyst for acrolein production and heated to 320° C. The exit of the above reaction tube for the oxidative dehydrogenation step was linked to the entrance of the reactor for the first oxidation step with steel piping, and kept at 350° C. Through the entrance of the reactor, the exit gas (B) from the oxidative dehydrogenation step was supplied and the reaction gas was discharged through the exit of the reactor. [This gas is referred to as the exit gas (C)].

[The Second Oxidation Step]

A shell-and-tube reactor for the second oxidation step, comprising two steel tubes of 25 mm in inner diameter and 3000 mm in length each, was uniformly charged with 2.5 L of the catalyst for acrylic acid production and heated to 260° C. The exit of the above reactor for the first oxidation step was linked to the entrance of the reactor for the second oxidation step with steel piping, and kept at 170° C. Through the entrance of the reactor, the exit gas (C) from the first oxidation step was supplied and the reaction gas was discharged through the exit of the reactor. [This gas is referred to as the exit gas (D)].

[The Acrylic Acid Recovery Step]

Then the exit gas (D) from the second oxidation step was introduced into an acrylic acid collection device, and the aqueous acrylic acid solution (E) was collected at 50° C. [The gas which was discharged from the acrylic acid collection device in this occasion is referred to as the gas (F).] Where necessary, a polymerization inhibitor containing hydroquinone as the chief component was added to the aqueous acrylic acid solution (E).

[The Carbon Dioxide-Removing Step]

The gas (F) discharged from the acrylic acid recovery step was pressurized to 1.5 MPa, and thereafter introduced into a carbon dioxide absorption column.

In the carbon dioxide absorption column, the discharged gas was contacted with 35% aqueous potassium carbonate solution which was superheated to about 100° C., to cause the carbon dioxide absorption. A part of the gas (G) which was discharged from the carbon dioxide absorption column was purged, and the remainder was recirculated for re-use at the oxidative dehydrogenation step as the recycling gas.

The aqueous potassium carbonate solution which absorbed the carbon dioxide was sent to a carbon dioxide desorption column and after being desorbed of carbon dioxide at the same column, was used again at the carbon dioxide absorption column.

After the steady state was attained, the purge ratio of the gas (G) as discharged from the carbon dioxide absorption column was 5 vol %, and the compositions of the gases at respective sites were as shown in Table 1, in which liquefied matters were calculated as hypothetically gasified.

The theoretical acquisition amount of acrylic acid was 921 g/hr, and the acrylic acid yield was 62.4 mol %.

TABLE 1

| | Composition of Gas at Respective Sites (vol %) | | | | | | |
|---|---|---|---|---|---|---|---|
| | (A) | (B) | (C) | (D) | (E) | (F) | (G) |
| Propane | 39.3 | 25.0 | 21.7 | 22.5 | 2.0 | 30.8 | 36.0 |
| Propylene | 0.3 | 8.4 | 7.3 | 0.3 | 0.0 | 0.4 | 0.4 |
| Acrylic acid | 0.1 | 0.4 | 0.4 | 7.5 | 22.3 | 0.4 | 0.1 |
| Oxygen | 18.2 | 1.3 | 14.1 | 1.5 | 0.0 | 2.1 | 2.5 |
| Water | 3.0 | 21.5 | 18.7 | 27.7 | 74.4 | 10.2 | 4.4 |
| CO | 26.9 | 27.0 | 23.5 | 23.7 | 0.0 | 33.2 | 39.0 |
| CO$_2$ | 9.6 | 13.3 | 11.5 | 14.3 | 0.4 | 19.7 | 13.9 |
| Acetic acid | 0.0 | 0.1 | 0.1 | 0.3 | 0.9 | 0.0 | 0.0 |
| Acrolein | 0.1 | 0.7 | 0.6 | 0.1 | 0.0 | 0.2 | 0.2 |
| Argon | 2.5 | 2.3 | 2.1 | 2.1 | 0.0 | 3.0 | 3.5 |

Comparative Example 1

Example 1 was repeated except that the gas (F) discharged from the acrylic acid collection device was not introduced into the carbon dioxide absorption column, but was recirculated to the oxidative dehydrogenation step for re-use, after a part thereof was purged.

Upon initiation of the reaction, carbon dioxide started to accumulate in the reaction system, and increase in the pressure inside the system was observed. The supply rate of the starting gaseous mixture (a gaseous mixture of 44.5 vol % of propane, 55.3 vol % of oxygen and the balance of argon), therefore, was decreased to 406 L/hr (standard state), and an approximately stable condition was attained. The purge ratio of the gas (F) discharged from the acrylic acid collection device at that time was 5 vol %, and the compositions of the gases at the respective sites were as shown in Table 2. The theoretical acquisition amount of acrylic acid was 374 g/hr and the acrylic acid yield was 64.3 mol %. As compared with Example 1, the theoretical acquisition amount of acrylic acid was at a very low level.

TABLE 2

| | Composition of Gas at Respective Sites (vol %) | | | | | |
|---|---|---|---|---|---|---|
| | (A) | (B) | (C) | (D) | (E) | (F) |
| Propane | 16.0 | 10.7 | 10.0 | 10.2 | 0.8 | 11.9 |
| Propylene | 0.1 | 3.6 | 3.4 | 0.1 | 0.0 | 0.1 |
| Acrylic acid | 0.4 | 0.5 | 0.5 | 3.8 | 22.8 | 0.5 |
| Oxygen | 8.7 | 1.8 | 7.5 | 1.6 | 0.0 | 1.9 |
| Water | 9.0 | 16.7 | 15.7 | 19.7 | 74.0 | 10.3 |
| CO | 11.0 | 11.6 | 10.9 | 10.8 | 0.0 | 12.6 |
| $CO_2$ | 53.7 | 53.8 | 50.7 | 52.6 | 1.4 | 61.4 |
| Acetic acid | 0.0 | 0.0 | 0.0 | 0.2 | 1.0 | 0.0 |
| Acrolein | 0.1 | 0.3 | 0.3 | 0.0 | 0.0 | 0.1 |
| Argon | 1.0 | 1.0 | 1.0 | 0.0 | 0.0 | 1.2 |

Comparative Example 2

Comparative Example 1 was run as above, but when the pressure increase in the system was observed, stabilization of the inside pressure was attempted by changing the purge ratio, instead of decreasing the supply of the starting gaseous mixture as done in Comparative Example 1. When the inside pressure came to be nearly stabilized, further a gaseous mixture of 50.3 vol % of propane, 49.5 vol % of oxygen and the balance of argon was supplied at a rate of 912 L/hr (standard state), to optimize the oxygen supply. An to approximately steady state was attained. The purged ratio at that time was 14.7%, and the compositions of the gases at the respective sites were as shown in Table 3. The theoretical acquisition amount of acrylic acid was 779 g/hr and the acrylic acid yield was 52.9 mol %. As compared with Example 1, the theoretical acquisition amount and the yield of acrylic acid decreased.

TABLE 3

| | Composition of Gas at Respective Sites (vol %) | | | | | |
|---|---|---|---|---|---|---|
| | (A) | (B) | (C) | (D) | (E) | (F) |
| Propane | 33.6 | 21.6 | 19.2 | 19.8 | 1.7 | 27.0 |
| Propylene | 0.2 | 7.3 | 6.5 | 0.2 | 0.0 | 0.3 |
| Acrylic acid | 0.3 | 0.6 | 0.5 | 6.8 | 22.8 | 0.4 |
| Oxygen | 15.6 | 1.1 | 12.3 | 1.4 | 0.0 | 2.0 |
| Water | 7.3 | 23.0 | 20.4 | 28.2 | 73.5 | 10.2 |
| CO | 10.7 | 11.9 | 10.6 | 10.8 | 0.0 | 15.0 |
| $CO_2$ | 31.5 | 33.2 | 29.4 | 31.8 | 1.0 | 44.1 |
| Acetic acid | 0.0 | 0.0 | 0.0 | 0.3 | 1.0 | 0.0 |
| Acrolein | 0.1 | 0.6 | 0.5 | 0.1 | 0.0 | 0.1 |
| Argon | 0.7 | 0.7 | 0.6 | 0.6 | 0.0 | 0.9 |

The invention claimed is:

1. A process for producing acrylic acid from propane as the starting material, characterized by comprising the following steps (a)-(f):
   (a) an oxidative dehydrogenation step of passing a gaseous starting mixture containing propane and molecular oxygen through a propylene synthesis zone to form a first flow containing propylene, wherein the supply source of the molecular oxygen has an oxygen concentration higher than 21% by volume;
   (b) a first oxidation step of passing the first flow through an acrolein synthesis zone to form a second flow containing acrolein;
   (c) a second oxidation step of passing the second flow through an acrylic acid synthesis zone to form a third flow containing acrylic acid;
   (d) an acrylic acid recovery step of separating the third flow to a liquid flow containing acrylic acid and a gaseous fourth flow containing unreacted propane and carbon dioxide;
   (e) a carbon dioxide-removing step of selectively eliminating at least a part of the carbon dioxide from the fourth flow to form a fifth flow containing unreacted propane; and
   (f) a recycling step of re-using at least a part of the fifth flow as a recycling gas.

2. The process for producing acrylic acid according to claim 1, characterized by circulating at least a part of the fifth flow to at least one of the step (a), step (b) and step (c).

3. The process for producing acrylic acid according to claim 1, characterized by supplying further molecular oxygen to the step (b) and/or step (c).

4. The process for producing acrylic acid according to claim 2, characterized by supplying further molecular oxygen to the step (b) and/or step (c).

5. The process for producing acrylic acid according to claim 1, wherein the carbon dioxide is selectively eliminated in step (e) through a carbon dioxide absorption step and a carbon dioxide desorption step.

* * * * *